US00PP28437P3

(12) United States Plant Patent
Brazelton et al.

(10) Patent No.: US PP28,437 P3
(45) Date of Patent: Sep. 26, 2017

(54) BLUEBERRY PLANT NAMED 'FCM12-097'

(50) Latin Name: ***Vaccinium corymbosum* hybrid**
Varietal Denomination: FCM12-097

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 38 days.

(21) Appl. No.: 14/998,607

(22) Filed: Jan. 21, 2016

(65) Prior Publication Data

US 2016/0219765 P1 Jul. 28, 2016

Related U.S. Application Data

(60) Provisional application No. 62/125,498, filed on Jan. 23, 2015.

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — June Hwu
(74) *Attorney, Agent, or Firm* — Hahn Loeser & Parks, LLP-San Diego

(57) ABSTRACT

The new blueberry plant variety 'FCM12-097' is provided. 'FCM12-097' is a commercial variety intended for the hand harvest fresh market. The variety is produced from a cross of 'FF03-194' and 'FL00-180'. 'FCM12-097' can be distinguished by its outstanding features of producing large fruit with a small picking scar on current season's growth, a moderately branched growth habit, low vigor, very widely spaced internodes, wide leaves with a rounded base, urceolate flowers, and large, light blue fruit with a moderately flattened shape.

7 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'FCM12-097'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FCM12-097', as herein described and illustrated. 'FCM12-097' is a compact plant that produces, large, firm fruit with a small dry picking scar under evergreen production systems in Central Mexico. The climactic conditions of Central Mexico represent a challenge to growing traditional low chill blueberry varieties. Under these conditions, many traditional low-chill blueberry varieties (developed in latitudes 25°-35°) do not produce flower buds or flowers. For those blueberry varieties that do flower under these conditions, the flowers are produced primarily on current season's growth that is often referred to as a 'primocane' in the blueberry industry. The 'primocane' inflorescences tend to be very elongated in form compared to the inflorescence produced at higher latitudes from dormant buds, and the fruit often does not abscise well from the pedicel, resulting in a large picking scar, which greatly limits shelf life. The blueberry industry in this area is dominated by the variety 'Biloxi'. 'Biloxi' is one of the few traditional low chill varieties that grows well and produces fruit with a good picking scar in this growing environment. However, 'Biloxi' often produces an excessive proportion of small, unmarketable fruit. 'FCM12-097' was exceptional because it flowered and fruited more than most genotypes but also had large, firm fruit with a small picking scar.

SUMMARY OF THE INVENTION

Pedigree and History: The new blueberry plant originated from a cross made in 2008 of 'FF03-194' (female parent, unpatented) by 'FL00-180' (pollen parent, unpatented), made in Lowell, Oreg.

The cross that produced 'FCM12-097' (denominated by the cross code X08-167) was made in Lowell, Oreg., USA in 2008.

The new blueberry plant variety 'FCM12-097' was initially propagated by softwood cuttings in 2012. Rooted plants from these cuttings were field planted in Tala, Jalisco, Mexico and also shipped to Lowell, Oreg., USA in 2013. Additional plants have been propagated via softwood cuttings from the plants established in Tala, Mexico in 2014. The plants sent to Lowell, Oreg. were also propagated via softwood cuttings in 2014 and successfully used to establish in vitro culture lines in 2014.

The seedling family that produced 'FCM12-097' was initially grown in 50 cell propagation trays and shipped to Mexico in March, 2011 after the plants had reached sufficient size to be field planted. They were planted in a commercial blueberry field near Colima City, state of Colima, Mexico and evaluated for fruit production and quality beginning in December 2011. 'FCM12-097' was selected in 2012 because it flowered well in a zero chill, evergreen production system and produced fruit with very large size, firm texture, good flavor, and a small picking scar. After being selected in Colima, 'FCM12-097' was propagated by softwood cuttings and a ten plant plot was established in Tala, Jalisco, Mexico (near the capital city Guadalajara). The ten plant plot was evaluated for fruit quality and yield in comparison to the standard varieties 'Biloxi' and 'Ventura' (U.S. Plant Pat. No. 24,606) beginning in December, 2013. After two harvest seasons of evaluation, the yield and fruit quality of 'FCM12-097' were deemed sufficiently good to warrant launching it as a commercial variety.

The new blueberry plant 'FCM12-097' as it grows in Tala, Mexico is distinguished by a moderately branching growth habit, moderate vigor, very widely spaced internodes, wide leaves with a rounded base, urceolate flowers, and large, light blue fruit with a moderately flattened shape. The new blueberry plant 'FCM12-097' consistently produces much larger fruit than the standard variety 'Biloxi', which is a very desirable characteristic. The following characteristics of the new cultivar have been repeatedly observed and can be used to distinguish 'FCM12-097' as a unique *Vaccinium corymbosum* hybrid plant:

1) Flattened (oblate) fruit that is firm, light blue in color, and consistently larger than the cultivar 'Biloxi'
2) Small picking scar on fruit derived from the current season's growth
3) Widely spaced internodes
4) Wide leaves with a rounded base Plants of 'FCM12-097' propagated from softwood cuttings or in vitro are phenotypically stable and exhibit the same characteristics as the original plant. During flushes of new growth following pruning or in spring, 'FCM12-097' leaves may sometimes exhibit a variegated green and white pattern. The variegated pattern typically fades as the leaves darken and attain full size. This trait is only expressed transiently but has been observed in all propagated material of 'FCM12-097'. The parent 'FF03-194' was evaluated at the same location in Colima, Mexico where the seedling of 'FCM12-097' was originally selected. In Colima, 'FF03-194' had poor plant vigor, strongly evergreen leaves, and shorter internode lengths than 'FCM12-097'. The arrangement of the fruit clusters, the size and shape of the fruit on 'FF03-194' was similar to that of 'FCM12-097' in Colima. 'FF03-194' may also possess variegated foliage on new growth, like 'FCM12-097'. However the fruit of 'FF03-194' is darker blue in color, has larger, more irregularly shaped sepals, and has a larger picking scar than 'FCM12-097'. The parent 'FL00-180' has not been evaluated in the same environment of Mexico that 'FCM12-097' was selected in. However, in California, USA 'FL00-180' was highly evergreen with large, firm, light blue fruit similar to 'FCM12-097'. The leaves of 'FL00-180' are less rounded with a more acute apex than 'FCM12-097'. The plant of 'FL00-180' also does not display the leaf variegation found in 'FCM12-097' and 'FF03-194'.

DETAILED BOTANICAL DESCRIPTION

Figure 1:
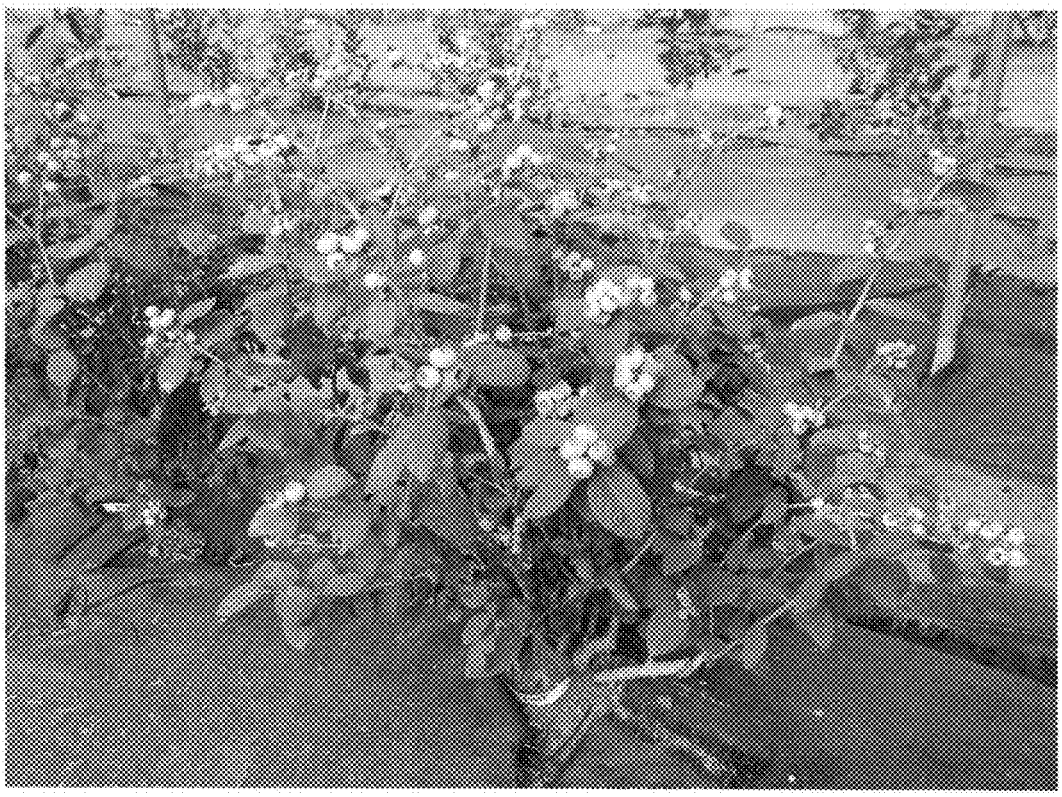
FIG. 1 is a photograph of the new variety 'FCM12-097' showing the plant's growth habit, overall shape and the distribution of fruit on the plant.
Figure 2:
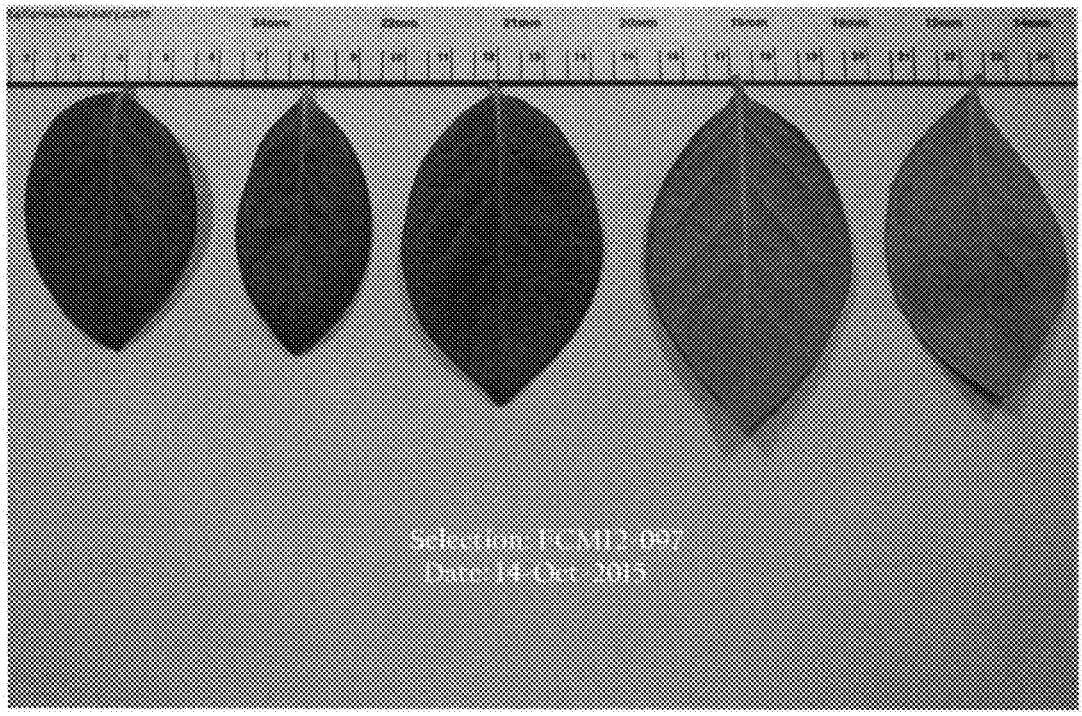
FIG. 2 is a photograph of leaves of the new variety 'FCM12-097' showing the wide leaves with rounded bases.
Figure 3:
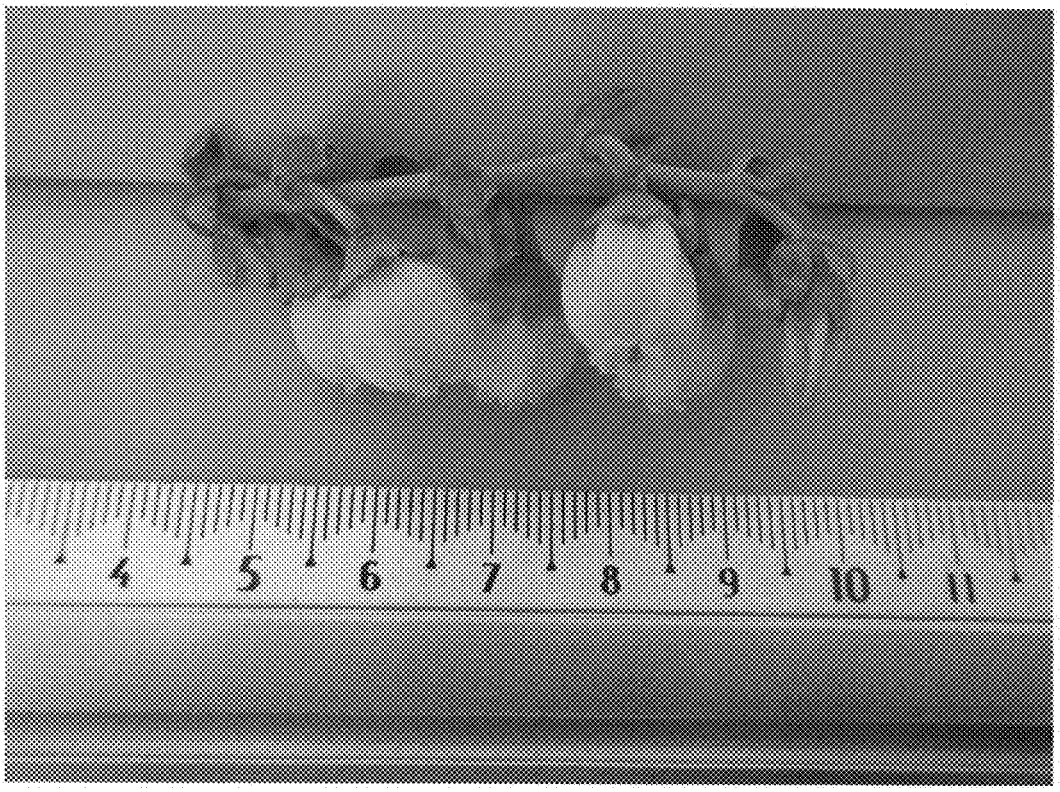
FIG. 3 is a photograph of the flowers of the new variety 'FCM12-097' showing the color and shape of the flowers.
Figure 4:
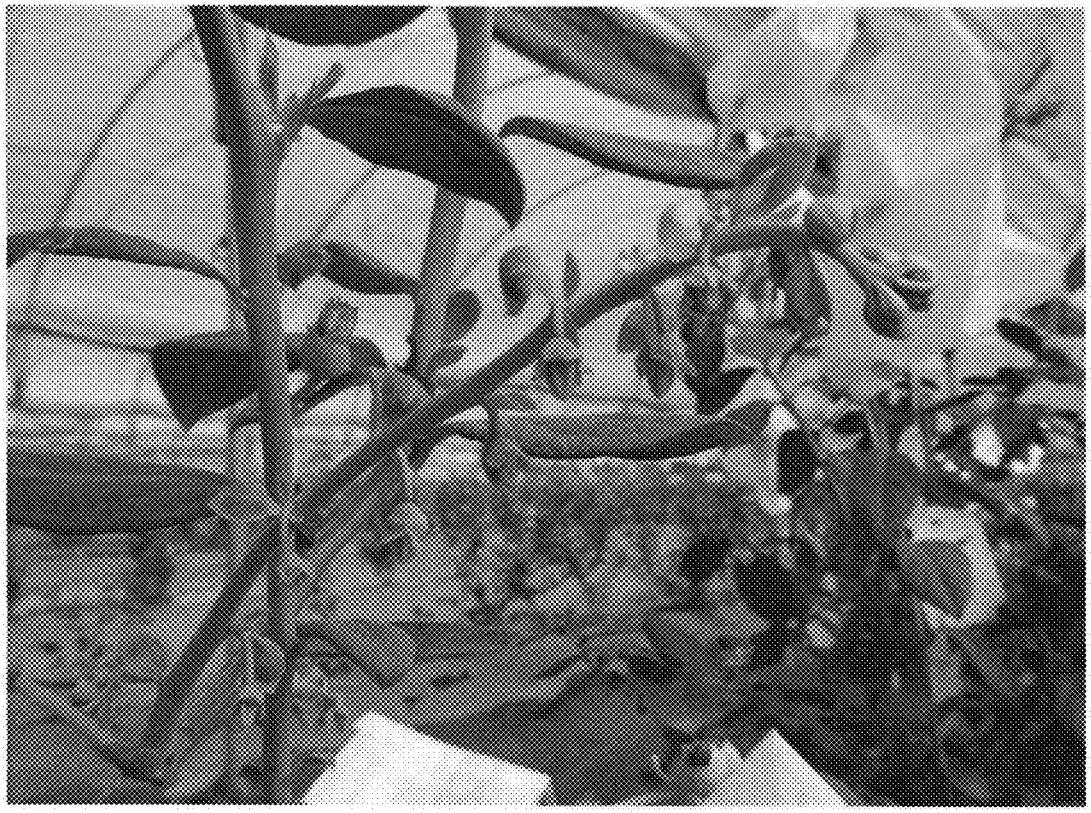
FIG. 4 is a photograph of an inflorescence of the new variety 'FCM12-097' derived from the current season's growth.
Figure 5:
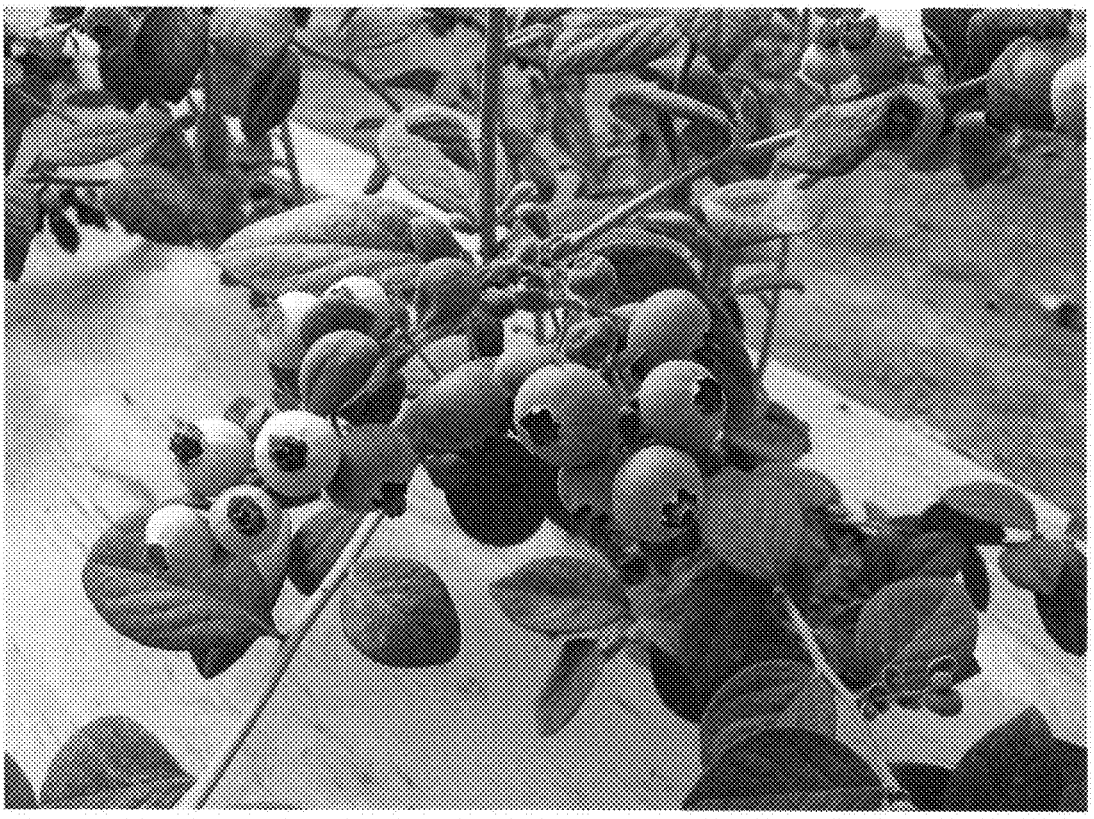
FIG. 5 is a photograph of a cluster of fruit of the new variety 'FCM12-097' showing the arrangement of the fruit on the plant.
Figure 6:
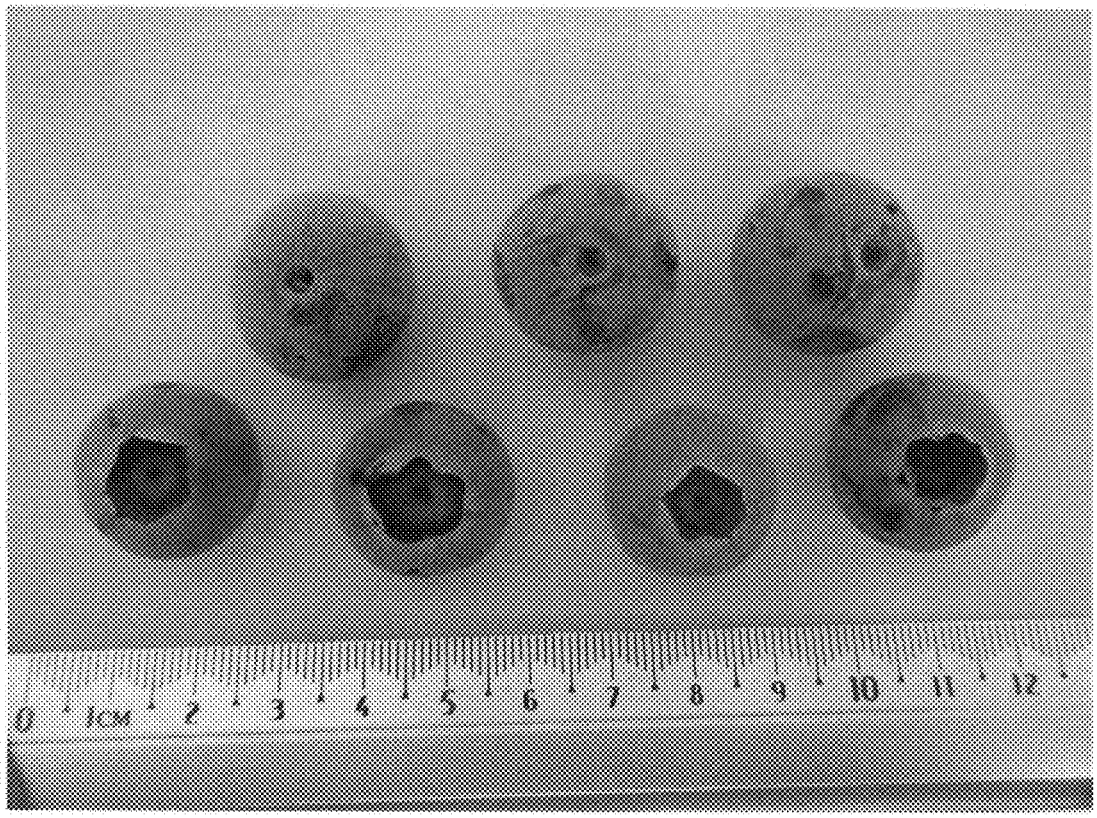
FIG. 6 is a photograph of the fruit of the new variety 'FCM12-097' showing the size, shape, and color of the fruit.
Figure 7:
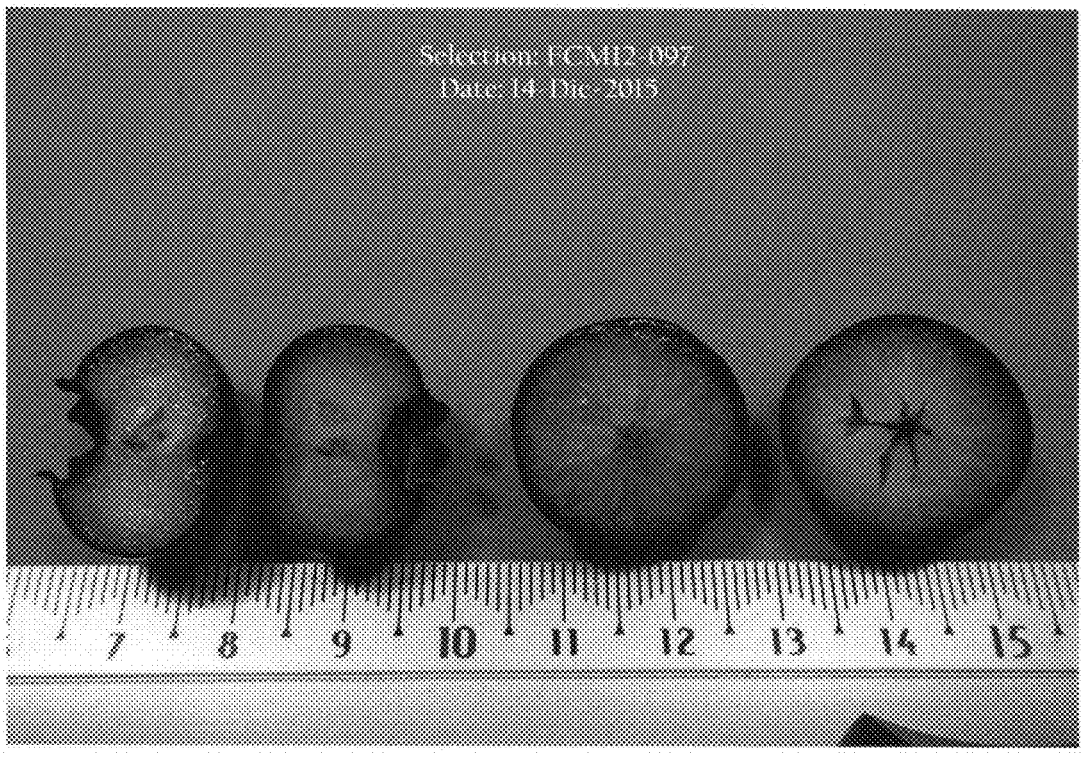
FIG. 7 is a photograph of the fruit of the new variety 'FCM12-097' in cross-section, showing the shape of the fruit and the depth of the calyx basin.

The following detailed description sets forth the distinctive characteristics of 'FCM12-097'. The data which defines these characteristics were collected from asexual reproductions of the original selection. Dimensions, sizes, colors, and other characteristics are approximations and averages set forth as accurately as possible. The plant history was taken on plants approximately three years of age, and the descriptions relate to plants grown in the field in Tala, Jalisco, Mexico. Descriptions of fruit characteristics were made on fruit grown in Tala, Jalisco, Mexico. Color designations are from "The Pantone Book of Color" (by Leatrice Eiseman and Lawrence Herbery, Harry N. Abrams, Inc., Publishers, New York 1990). Where the Pantone color designations differ from the colors in the photographs, the Pantone colors are accurate.

VARIETY:

Classification:

*a. Family.*—Ericaceae.
*b. Genus.*—*Vaccinium.*
*c. Species.*—*corymbosum* hybrid.
*d. Common name.*—Southern Highbush Blueberry.

Parentage:

*a. Female parent.*—'FF03-194' (unpatented).
*b. Male parent.*—'FL00-180' (unpatented, owned by University of Florida and used with permission).

Market class: Commercial blueberry variety intended for the hand harvest fresh market.

PLANT

General:

*a. Parentage.*—Female parent 'FF03-194' (unpatented) Male parent 'FL00-180' (unpatented).
*b. Plant height.*—3 year old plants average 78.2 cm in height.
*c. Plant width.*—3 year old plants average 78.2 cm in height.
*d. Growth habit.*—Semi-erect, moderately branched, rounded in shape.
*e. Plant vigor.*—Low.
*f. Productivity.*—In Tala, state of Jalisco, Mexico, 1 year old plants produced 0.72 kilos of fruit per plant and 2 year old plants produced 2.29 kilos per plant. In comparison, 1 year old plants of 'Biloxi' produced 0.56 kilos of fruit per plant, and 2 year old plants of 'Biloxi' produced 2.12 kilos of fruit per plant.

g. *Suitability for mechanical harvesting*.—Low, due to plant growth habit and prolonged fruit ripening period.
h. *Cold hardiness*.—Not evaluated but likely poor, estimated at USDA zone 8.
i. *Chilling requirement*.—Not evaluated but estimated at 400 hours below 7° C.
j. *Leafing*.—Low.
k. *Twigginess*.—Low.
l. *Resistance/susceptibility to root rot* (*Phytopthora cinnamomi*).—Does not appear to be overly susceptible.
m. *Resistance/susceptibility to stem blight* (*Botryosphaeria sp.*).—Does not appear to be overly susceptible.
n. *Resistance/susceptibility to Phomopsis twig blight* (*Phomopsis vaccinii*).—Not evaluated.
o. *Resistance/susceptibility to Botrytis* (*Botrytis cinerea*).—Does not appear to be overly susceptible.
p. *Resistance/susceptibility to leaf spot* (*Septoria spp.*).—Not evaluated.
q. *Resistance/susceptibility to leaf rust* (*Naohidemyces vaccinii*).—Does not appear to be overly susceptible
r. *Resistance/susceptibility to bud mites* (*Acalitus vaccinii*).—Not evaluated.

STEM

General:
a. *Suckering tendency*.—Low.
b. *Mature cane color*.—Willow 16-0632 and Russet Brown 19-1338.
c. *Mature cane length*.—Average 28 cm.
d. *Mature cane width*.—Average 6.6 cm.
e. *Bark texture*.—Moderately rough.
f. *Fall color on new shoots*.—Not determined. Not applicable in evergreen production system where plants do not enter dormancy.
g. *Surface texture of new wood*.—Smooth.
h. *Internode length on strong, new shoots*.—Average 20.35 mm.
i. *Average number of buds per fruiting lateral*.—Average 5.2 buds.

FOLIAGE

General:
a. *Time of beginning of leaf bud burst*. —Not determined. Not applicable in evergreen production system where plants do not enter dormancy.
b. *Leaf color* (*top side*).—Chive 19-0323.
c. *Leaf color* (*under side*).—Mistletoe 16-0220.
d. *Leaf arrangement*.—Alternate.
e. *Leaf shape*.—Elliptical.
f. *Leaf margins*.—Entire.
g. *Leaf venation*.—Anastomosing.
h. *Leaf apices*.—Acute or slightly acuminate.
i. *Leaf bases*.—Rounded.
j. *Leaf length*.—Average 72.03 mm.
k. *Leaf width*.—Average 43.82 mm.
l. *Leaf length/width ratio*.—Low (1.64).
m. *Leaf nectaries*.—Absent.
n. *Pubescence of upper side*.—Absent.
o. *Pubescence of lower side*.—Absent.
p. *Cross sectional profile*.—Undulate.
q. *Longitudinal profile*.—Semi-revolute.
r. *Attitude*.—Porrect.

Petioles:
a. *Length*.—Average 3.93 mm.
b. *Width*.—Average 2.22 mm.
c. *Color*.—Peridot 17-0336.
d. *Surface texture*.—Smooth, slightly rough at base.

FLOWERS

General:
a. *Time of beginning of flowering*.—October 12 (In Tala, Jalisco, Mexico following a heavy pruning on May 22).
b. *Time of* 50% *anthesis*.—October 22 (In Tala, Jalisco, Mexico following a heavy pruning on May 22) .
c. *Flower shape*.—Urceolate.
d. *Flower fragrance*.—Faint, fresh.
e. *Immature flower color*.—Hay 12-0418.
f. *Pollen staining*.—Not evaluated.
g. *Self-compatibility*.—Probably good. Self-pollinated flowers averaged 76% fruit set and 4.2 seeds per berry, compared to cross-pollinated flowers that average 77% fruit set and 2.2 seeds per berry. FCM12-097 is also highly parthenocarpic when grown in Jalisco, Mexico and most mature fruit contain few or no seeds.

Corolla:
a. *Color*.—Winter White 11-0507.
b. *Length*.—Average 9.8 mm.
c. *Width*.—Average 10.8 mm.
d. *Aperture width*.—Average 5.97 mm.
e. *Anthocyanin coloration of corolla at time of anthesis*.—Low.
f. *Corolla ridges*.—Distinct.
g. *Protrusion of stigma*.—Average of 0.4 mm below lip of corolla (recessed).

Inflorescence:
a. *Length*.—Average 21.13 mm.
b. *Diameter*.—Average 26.96 mm.
c. *Length of peduncle*.—Average 38.14 mm.
d. *Surface texture of peduncle*.—Smooth.
e. *Color of peduncle*.—Oasis 16-0540.
f. *Length of pedicel*.—Average 9.59 mm.
g. *Surface texture of pedicel*.—Smooth.
h. *Color of pedicel*.—Green Banana 14-0434.
i. *Number of flowers per cluster*.—Average 7.4 flowers per cluster.
j. *Flower cluster density*.—Low.

Calyx (with sepals):
a. *Diameter*.—Average 6.19 mm.
b. *Color* (*sepals*).—Green Olive 17-0535.
c. *Calyx surface*.—Smooth.

Stamen:
a. *Length*.—Average 6.8 mm.
b. *Number per flower*.—Average 10.4.
c. *Filament color*.—Lily Green 13-0317.

Pistil:
a. *Length*.—Average 9.20 mm.
b. *Ovary color* (*exterior*).—Mistletoe 16-0220.
c. *Style*.—Length — average 8.31 mm.

Anther:
a. *Length*.—Average 4.40 mm.
b. *Number*.—Average 10.4.
c. *Color*.—Baked Clay 18-1441.

Pollen:
a. *Abundance*.—Low.
b. *Color*.—Alabaster 12-0812.

FRUIT

General:

*a. Time of fruit ripening.*—Early. Approximately November 24 in an evergreen production system in Jalisco, Mexico following a heavy pruning in May.

*b. Time of 50% maturity.*—Approximately February. In an evergreen production system, FCM12-097 flowers repeatedly and regularly, resulting in a sustained period of production for several months.

*c. Fruit development period.*—Approximately 45 days.

*d. Mean harvest date.*—Approximately February. In an evergreen production system, FCM12-097 flowers repeatedly and regularly, resulting in a sustained period of production for several months.

*e. Mean date last pick.*—In an evergreen production system, FCM12-097 will continue flowering until the plant is pruned or until it exhausts its nutrient supply. Typically the variety is pruned in May.

*f. Cluster density.*—Loose.

*g. Berries per cluster.*—Average 5.

*h. Unripe fruit color.*—Seacrest 13-0111.

*i. Ripe berry color.*—Lilac Gray 14-3903.

*j. Berry skin color after polishing.*—Shale 19-3903.

*k. Berry surface wax abundance.*—High.

*l. Berry flesh color.*—Lily Green 13-0317.

*m. Berry weight.*—Average 3.0 grams.

*n. Berry height from calyx to scar.*—Average 13.97 mm.

*o. Berry diameter.*—Average 18.33 mm.

*p. Calyx aperture.*—Average 6.44 mm.

*q. Calyx depth.*—Average 3.4 mm.

*r. Pedicel length.*—Average 10.57 mm.

*s. Pedicel surface texture.*—Smooth.

*t. Berry detachment force.*—Medium.

*u. Berry shape.*—Oblate.

*v. Fruit stem scar.*—Medium, dry.

*w. Berry flavor.*—Mild, slightly tart.

*x. Sweetness when ripe.*—Medium.

*y. Firmness when ripe.*—Excellent.

*z. Acidity when ripe.*—Medium to high.

*aa. Storage quality.*—Excellent, over 3 weeks at 0° C.

*bb. Uses.*—Primarily fresh market.

SEED

General:

*a. Seed abundance in fruit.*—Very low (often parthenocarpic in Jalisco).

*b. Seed color.*—Hazel 17-1143.

*c. Seed dry weight.*—Not measured (unable to harvest sufficient number of seeds for a proper average due to parthenocarpic fruit development).

*d. Seed length.*—Average 2.01 mm.

COMPARISON BETWEEN PARENTAL AND COMMERCIAL CULTIVARS

| Selection | Foliage | Fruit shape and color | Fruit firmness | Fruit size |
|---|---|---|---|---|
| FCM12-097 | Wide leaves, sometimes variegated, very widely spaced internodes | Oblate, light blue | Excellent | Very large |
| FF03-194 | Wide leaves, Moderately spaced internodes, sometimes variegated | Oblate, dark blue | Medium | Medium to Large |
| FL00-180 | Less rounded with more acute apex than FCM12-097 | Oblate, light blue | Excellent | Large to Very Large |
| 'Ventura' | Moderately narrow, very elliptical leaves, widely spaced internodes | Globose, light blue | Good | Medium to Large |
| 'Biloxi' | Short, wide leaves with round or obtuse apex and very closely spaced internodes | Globose or slightly oblate | good | Medium |

The invention claimed is:

1. A new and distinct variety of blueberry plant named 'FCM12-097' substantially as illustrated and described herein.

* * * * *